United States Patent
Fan et al.

(10) Patent No.: US 12,383,571 B2
(45) Date of Patent: Aug. 12, 2025

(54) METHOD FOR ENHANCING TYROSINASE INHIBITORY ACTIVITY

(71) Applicant: Jiangnan University, Wuxi (CN)

(72) Inventors: Liuping Fan, Wuxi (CN); Qun Yu, Wuxi (CN); Jinwei Li, Wuxi (CN)

(73) Assignee: Jiangnan University, Wuxi (CN)

( * ) Notice: Subject to any disclaimer, the term of this patent is extended or adjusted under 35 U.S.C. 154(b) by 863 days.

(21) Appl. No.: 17/546,180

(22) Filed: Dec. 9, 2021

(65) Prior Publication Data

US 2022/0096506 A1    Mar. 31, 2022

Related U.S. Application Data

(63) Continuation of application No. PCT/CN2019/092511, filed on Jun. 24, 2019.

(30) Foreign Application Priority Data

Jun. 19, 2019 (CN) .......................... 201910529625.X

(51) Int. Cl.
*A61K 31/704* (2006.01)
*A61K 31/192* (2006.01)
*A61K 31/352* (2006.01)

(52) U.S. Cl.
CPC .......... *A61K 31/704* (2013.01); *A61K 31/192* (2013.01); *A61K 31/352* (2013.01)

(58) Field of Classification Search
CPC ... A61K 31/704; A61K 31/192; A61K 31/352
USPC ........................................................ 514/33
See application file for complete search history.

(56) References Cited

PUBLICATIONS

Lee et al., Published Jun. 30, 2012, Food Science and Biotechnology, vol. 21 pp. 815-822 (Year: 2012).*
Liang et al., Published Mar. 7, 2012, Food Chemistry, vol. 134, pp. 1146-1148 (Year: 2012).*
Wang et al., Published Dec. 30, 2010, Food Chemistry, vol. 127, Issue 1, pp. 141-146 (Year: 2010).*
Cheng et al., Published Nov. 20, 2013, Evidence-Based Complementary and Alternative Medicine, vol. 2013, Issue 1, pp. 1-10 (Year: 2013).*
E.J. Lee et al., Published Oct. 7, 2010, Journal of Food Science, vol. 75, Issue 9, pp. C703-C709 (Year: 2010).*
Qun Yua et.al. "Five individual polyphenols as tyrosinase inhibitors: Inhibitory activity synergistic effect action mechanism and molecular docking.", Food Chemistry, vol. 297,May 27, 2019.
Chun Liang et. al., "Dioscin: A synergistic tyrosinase inhibitor from the roots of Smilax china.", Food Chemistry, vol. 134, Mar. 7, 2012.

* cited by examiner

*Primary Examiner* — Renee Claytor
*Assistant Examiner* — Jaret J Crews
(74) *Attorney, Agent, or Firm* — IPRO, PLLC

(57) ABSTRACT

The disclosure provides a method for enhancing tyrosinase inhibitory activity, and belongs to the technical field of intensive and deep processing of fruits and vegetables. The disclosure improves an inhibitory effect of a tyrosinase inhibitor on tyrosinase in manner of heating treatment; the tyrosinase inhibitor consists of a phenolic acid with a concentration of 0.6-1.8 mg/mL and a saponin with a concentration of 0.5-1.5 mg/mL; and the heating treatment conditions are as follows: the heating temperature is 130-170° C., and the heating time is 30-120 min. The disclosure compounds polyphenols and the saponin into the tyrosinase inhibitor, tyrosinase relative activity after treatment can be as low as 5%, and a three-component polyphenol can produce a synergistic effect; high temperature will make the saponin deglycosylated to produce substances with a powerful tyrosinase inhibitory effect, such as a polyphenol polymer, thus greatly improving the inhibitory effect of the tyrosinase inhibitor on the tyrosinase.

20 Claims, 1 Drawing Sheet

METHOD FOR ENHANCING TYROSINASE INHIBITORY ACTIVITY

TECHNICAL FIELD

The disclosure relates to a method for enhancing tyrosinase inhibitory activity, and belongs to the technical field of intensive and deep processing of fruits and vegetables.

BACKGROUND

Tyrosinase is a key rate-limiting enzyme for melanin formation in a bacterium, a fungus, a plant, a mammal and a human body, which is one of reasons for browning of fresh fruits and vegetables and beverages and production of the melanin in human skin. While a tyrosinase inhibitor can effectively reduce production of melanin and browning in a food system by inhibiting tyrosinase activity, thereby reducing an adverse effect caused by the tyrosinase, and therefore, in recent years, with the tyrosinase inhibitor being continuously discovered, its research and development have also received increasing attention. Phenolic substances (quercetin, ferulic acid and cinnamic acid) and saponins (dioscin and protodioscin) are common active ingredients in fruit and vegetable products, which have functions of anxiety resistance, diuresis, improving sleep quality, lowering blood sugar, tumor resistance, improving memory, aging resistance, reducing dysphoria and fatigue and the like, and meanwhile, they also have a significant effect in whitening.

Existing tyrosinase inhibitors are mainly divided into animal sources (silk gum, a collagen peptide, etc.), plant sources (platycodin, myricetin, catechin, aloin, etc.), microbial sources (*Botrytis cinerea*, kojic acid, etc.), chemical synthetics (vitamin C, superoxide dismutase, hydrogen peroxide, etc.) according to their sources. At present, research on a tyrosinase inhibitor mainly focuses on effects of single active ingredients on tyrosinase activity, a synthetic compound of which has a relatively strong side effect, while a natural active ingredient has a characteristic that its inhibitory effect is not significant.

SUMMARY

In view of the above problems, the disclosure takes quercetin, a cinnamic acid and a ferulic acid as representative polyphenols and protodioscin and dioscin as representative saponins, and improves its inhibitory effects on tyrosinase in manner of heating treatment.

The first object of the disclosure is to provide a method for enhancing tyrosinase inhibitory activity, which improves an inhibitory effect of a tyrosinase inhibitor on the tyrosinase in manner of heating treatment; the tyrosinase inhibitor consists of a phenolic acid with a concentration of 0.6-1.8 mg/mL and a saponin with a concentration of 0.5-1.5 mg/mL; the heating treatment conditions are as follows: the heating temperature is 130-170° C., and the heating time is 30-120 min.

The second object of the disclosure is to provide a tyrosinase inhibitor, and the tyrosinase inhibitor consists of a phenolic acid with a concentration of 0.6-1.8 mg/mL and a saponin with a concentration of 0.5-1.5 mg/mL.

In an implementation method of the disclosure, the phenolic acid is three of quercetin, a cinnamic acid, a ferulic acid, a gallic acid, and isorhamnetin, including but not limited to the combinations as follows:
(a) the quercetin, the cinnamic acid and the ferulic acid;
(b) the quercetin, the gallic acid and the ferulic acid;
(c) the quercetin, the gallic acid and the isorhamnetin;
(d) the quercetin, the cinnamic acid and the isorhamnetin; and
(e) the quercetin, the ferulic acid and the isorhamnetin.

In an implementation method of the disclosure, the ratio of any three components of the phenolic acid is 1:(1-10):(1-10).

In an implementation method of the disclosure, the saponin includes one of protodioscin, dioscin, and sarsasapogenin.

The third objective of the disclosure is to provide an application of the tyrosinase inhibitor in terms of beauty and health care, pest control and food preservation.

The fourth object of the disclosure is to provide a compound having a function of inhibiting tyrosinase activity, and a structural formula of the compound is as shown in formula (I):

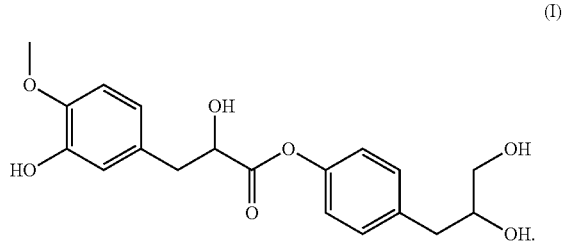 [SMILES: COc1ccc(CC(O)C(=O)Oc2ccc(CC(O)CO)cc2)cc1O]

The fifth object of the disclosure is to provide a tyrosinase inhibitor containing the above compound.

The beneficial effects of the disclosure are as follows:
(1) The disclosure compounds the polyphenols and the saponin into the tyrosinase inhibitor, all components have a certain synergistic effect in terms of inhibiting the tyrosinase activity, and tyrosinase relative activity after treatment can be as low as 5%;
(2) High temperature will make the saponin deglycosylated to produce substances with a powerful tyrosinase inhibitory effect, such as a polyphenol polymer, thus greatly improving the inhibitory effect of the tyrosinase inhibitor on the tyrosinase; and
(3) The disclosure has discovered a new compound having a function of inhibiting tyrosinase activity, which can be used as the tyrosinase inhibitor.

DETAILED DESCRIPTION

1. A determining method of tyrosinase activity: spectrophotometry is employed, 2.8 ml of 2.5 mM L-dopa solution is taken as a substrate, 100 μL of treated inhibitor solution is taken, then 100 μL of 0.2 mg/mL tyrosinase solution is added for incubation at 30° C. for 15 min, and then a change in its light absorption value is measured at 475 nm, and taking tyrosinase activity without an inhibitor as 100%, a calculation formula is as follows:

$$\text{tyrosinase relative activity}/\% = (B_2-B_1)/(A_2-A_1) \times 100,$$

Where $A_1$ and $A_2$ represent light absorption values of a blank group at 0 min and 15 min, and $B_1$ and $B_2$ represent light absorption values of a sample at 0 min and 15 min.

2. An evaluation method of interaction: with reference to literature such as Fan et al. (2017, Food & Function) and Cai et al. (2012, Journal of Agricultural and Food Chemistry), a specific method is as follows: 2.8 mL of 2.5 mM L-dopa solution is used as a substrate, 100 μL of inhibitor solutions different in treatment method and different in ratio is taken, then 100 μL of 0.2 mg/mL tyrosinase solution is added for incubation at 30° C. for 15 min, and then changes in its light absorption values are measured at 475 nm.

When Vab (or Vabc, Vabcd)−V*<−0.1, it is a synergistic effect (SY); when −0.1<Vab (or Vabc, Vabcd)−V*<+0.1, it is an additive effect (AD); and when Vab (or Vabc, Vabcd)−V*>+0.10, it is a sub-additive effect (SU).

Example 1

The technical solution of the disclosure includes steps as follows:
1) Uniformly mixing polyphenols: mixing quercetin, a cinnamic acid and a ferulic acid in a ratio of 5 mM quercetin+5 mM cinnamic acid+5 mM ferulic acid;
2) Uniformly mixing a saponin with the polyphenols: mixing the polyphenols in the step 1) with protodioscin with a concentration of 1.0 mg/mL;
3) Performing heating: performing heating treatment on a sample solution in the step 2) at 150° C. for 30 min; and
4) Determining its inhibitory effects on tyrosinase: diluting the above different treated solutions to different concentrations, and measuring its inhibitory effects on the tyrosinase by spectrophotometry. Results are shown in Table 1.

Figure 1:
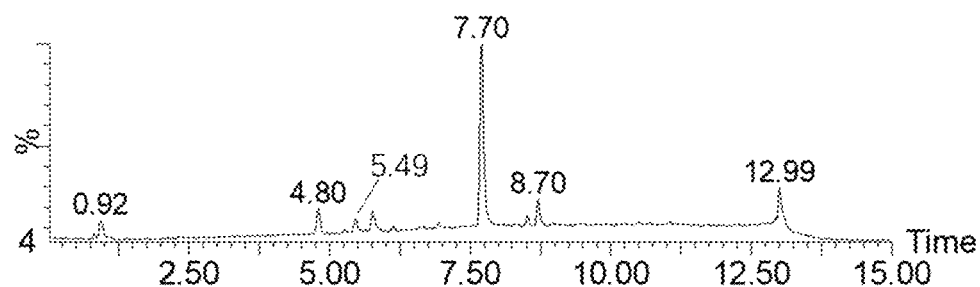
FIG. 1 is a liquid mass spectrogram of a mixture of quercetin, a cinnamic acid and a ferulic acid before being heated.
Figure 2:
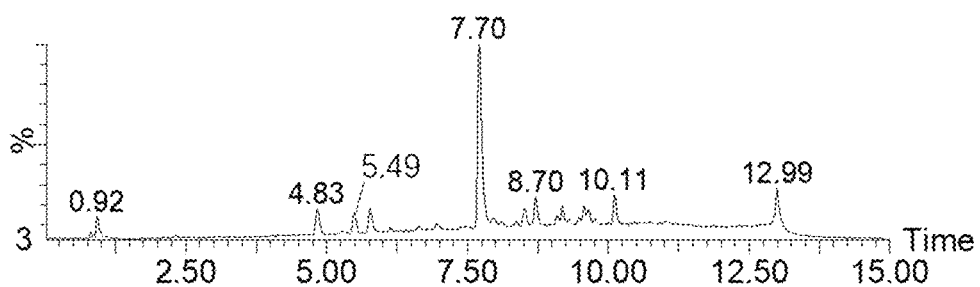
FIG. 2 is a liquid mass spectrogram of a mixture of quercetin, a ferulic acid and a cinnamic acid after being heated at 150° C. for 30 min.
Figure 3:
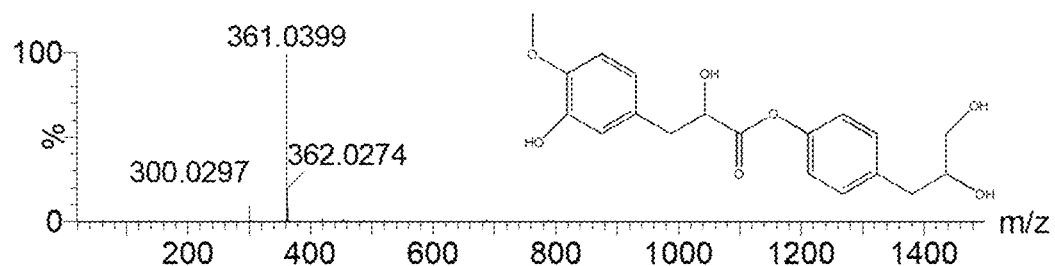
FIG. 3 shows a structural diagram of a new produced substance.

It can be seen from FIGS. 1 and 2 that a substance with retention time of 10.11 min is newly produced, under the heating conditions of 150° C. and 30 min, and it is inferred from the concentration that the substance may be a new substance produced by an esterification reaction of the ferulic acid. It can be seen from FIG. 3 that a structural formula of the new substance produced can be inferred as shown in formula (I):

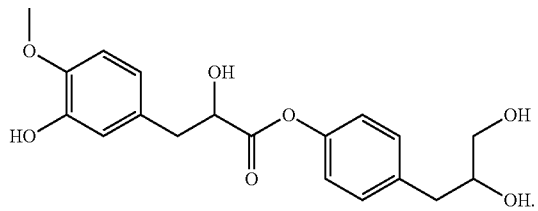

(I)

Example 2

The technical solution of the disclosure includes steps as follows:

1) Uniformly mixing polyphenols: mixing quercetin, a cinnamic acid and a ferulic acid in a ratio of 5 mM quercetin+0.5 mM cinnamic acid+5 mM ferulic acid;
2) Uniformly mixing a saponin with the polyphenols: mixing the polyphenols in the step 1) with protodioscin with a concentration of 0.5 mg/mL;
3) Performing heating: performing heating treatment on a sample solution in the step 2) at 150° C. for 30 min; and
4) Determining its inhibitory effects on tyrosinase: diluting the above different treated solutions to different concentrations, and measuring its inhibitory effects on the tyrosinase by spectrophotometry. Results are shown in Table 1.

Example 3

The technical solution of the disclosure includes steps as follows:
1) Uniformly mixing polyphenols: mixing quercetin, a gallic acid and a ferulic acid in a ratio of 5 mM quercetin+0.5 mM gallic acid+5 mM ferulic acid;
2) Uniformly mixing a saponin with the polyphenols: mixing the polyphenols in the step 1) with sarsasapogenin with a concentration of 1.5 mg/mL;
3) Performing heating: performing heating treatment on a sample solution in the step 2) at 130° C. for 30 min; and
4) Determining its inhibitory effects on tyrosinase: diluting the above different treated solutions to different concentrations, and measuring its inhibitory effects on the tyrosinase by spectrophotometry. Results are shown in Table 1.

Example 4

The technical solution of the disclosure includes steps as follows:
1) Uniformly mixing polyphenols: mixing quercetin, a gallic acid and isorhamnetin in a ratio of 5 mM quercetin+0.5 mM gallic acid+0.5 mM isorhamnetin;
2) Uniformly mixing a saponin with the polyphenols: mixing the polyphenols in the step 1) with protodioscin with a concentration of 1.0 mg/mL;
3) Performing heating: performing heating treatment on a sample solution in the step 2) at 170° C. for 30 min; and
4) Determining its inhibitory effects on tyrosinase: diluting the above different treated solutions to different concentrations, and measuring its inhibitory effects on the tyrosinase by spectrophotometry. Results are shown in Table 1.

Example 5

The technical solution of the disclosure includes steps as follows:
1) Uniformly mixing polyphenols: mixing quercetin, a cinnamic acid and isorhamnetin in a ratio of 5 mM quercetin+5 mM cinnamic acid+0.5 mM isorhamnetin; in an implementation method of the disclosure, the dosage of the quercetin, the ferulic acid and the isorhamnetin is 5 mM quercetin+5 mM ferulic acid+0.5 mM isorhamnetin;
2) Uniformly mixing a saponin with the polyphenols: mixing the polyphenols in the step 1) with protodioscin with a concentration of 1.0 mg/mL;
3) Performing heating: performing heating treatment on a sample solution in the step 2) at 150° C. for 30 min; and 4) Determining its inhibitory effects on tyrosinase: diluting the above different treated solutions to different concentrations, and measuring its inhibitory effects on the tyrosinase by spectrophotometry. Results are shown in Table 1.

Example 6

The technical solution of the disclosure includes steps as follows:
1) Uniformly mixing polyphenols: mixing quercetin, a ferulic acid and isorhamnetin in a ratio of 5 mM quercetin+5 mM ferulic acid+0.5 mM isorhamnetin;
2) Uniformly mixing a saponin with the polyphenols: mixing the polyphenols in the step 1) with protodioscin with a concentration of 1.0 mg/mL;
3) Performing heating: performing heating treatment on a sample solution in the step 2) at 150° C. for 30 min; and
4) Determining its inhibitory effects on tyrosinase: diluting the above different treated solutions to different concentrations, and measuring its inhibitory effects on the tyrosinase by spectrophotometry. Results are shown in Table 1.

TABLE 1

Effects of tyrosinase inhibitor on tyrosinase

| Tyrosinase inhibitor | Tyrosinase relative activity (%) | Vabc | $V^{*2}$ (Va × Vb × Vc) | Vabc − $V^{*2}$ | |
|---|---|---|---|---|---|
| Example 1 | 33.62 | 0.7870 | 0.9819 | −0.195 | SY |
| Example 2 | 48.71 | 0.7739 | 0.9039 | −0.130 | SY |
| Example 3 | 40.30 | 0.8196 | 0.9605 | −0.141 | SY |
| Example 4 | 44.23 | 0.7344 | 0.8724 | −0.138 | SY |
| Example 5 | 35.24 | 0.7252 | 0.8918 | −0.167 | SY |
| Example 6 | 35.33 | 0.7644 | 0.9467 | −0.182 | SY |

It can be seen from Table 1 that a synergistic effect can be produced by compounding any three phenolic acids. In addition, when the tyrosinase is treated by employing the tyrosinase inhibitor prepared by the method of the disclosure, the tyrosinase relative activity can be as low as 33.62%, and the tyrosinase inhibitor has a relatively good inhibitory effect on the tyrosinase.

Comparative Example 1: Effects of Tyrosinase Inhibitor with Different Components on Tyrosinase Inhibitory Activity 1. According to the method of Example 1, the difference is that the polyphenols are uniformly mixed according to polyphenol formulas in Tables 2-4, respectively, in the step 1), other parameter conditions are the same as those in Example 1, and its inhibitory effects on the tyrosinase are determined by the spectrophotometry. Results are shown in Tables 2-4.

It can be seen from Tables 2-4 that a single phenolic acid presents an activating effect on the tyrosinase, but when compounded with the quercetin, it presents a significant inhibitory effect. An inhibitor of a combination of a bi-component polyphenol and a four-component polyphenol can only achieve an additive effect, but cannot achieve a synergistic effect.

2. According to the method of Example 1, the difference is that a single phenolic acid is employed, that is, 5 mM quercetin, 5 mM cinnamic acid, 5 mM ferulic acid, 5 mM gallic acid, 5 mM isorhamnetin, and other parameter conditions are the same as those in Example 1, the determined tyrosinase relative activity (%) is 80.69%, 102.32%, 107.56%, 97.25%, and 82.52%, respectively.

TABLE 2

Effects of tyrosinase inhibitor consisting of bi-component polyphenol on tyrosinase

| Tyrosinase inhibitor | Tyrosinase relative activity (%) | Vab | $V^{*2}$ (Va × Vb) | Vab − $V^{*2}$ | |
|---|---|---|---|---|---|
| 5 mM quercetin + 5 mM ferulic acid | 105.95 | 1.0595 | 0.9402 | 0.119 | SU |
| 5 mM quercetin + 0.5 mM gallic acid | 101.42 | 1.0142 | 0.8672 | 0.147 | SU |
| 5 mM quercetin + 5 mM gallic acid | 109.35 | 1.0935 | 0.8213 | 0.272 | SU |
| 5 mM quercetin + 0.5 mM cinnamic acid | 107.65 | 1.0765 | 0.8161 | 0.260 | SU |
| 5 mM quercetin + 5 mM cinnamic acid | 98.58 | 0.9858 | 0.8865 | 0.099 | AD |
| 5 mM quercetin + 0.5 mM isorhamnetin | 102.55 | 1.0255 | 0.8547 | 0.171 | SU |

Note:
SY is the synergistic effect; AD is the additive effect; and SU is the sub-additive effect.

TABLE 3

Effects of tyrosinase inhibitor consisting of three-component polyphenol on tyrosinase

| Tyrosinase inhibitor | Tyrosinase relative activity (%) | Vabc | $V^{*2}$ (Va × Vb × Vc) | Vabc − $V^{*2}$ | |
|---|---|---|---|---|---|
| 5 mM quercetin + 5 mM gallic acid + 5 mM ferulic acid | 83.26 | 0.8326 | 0.9097 | −0.077 | AD |
| 5 mM quercetin + 0.5 mM gallic acid + 0.5 mM cinnamic acid | 88.26 | 0.8826 | 0.8330 | 0.050 | AD |
| 5 mM quercetin + 0.5 mM gallic acid + 5 mM cinnamic acid | 83.70 | 0.8370 | 0.9048 | −0.068 | AD |
| 5 mM quercetin + 5 mM gallic acid + 0.5 mM cinnamic acid | 89.35 | 0.8935 | 0.7889 | 0.105 | SU |
| 5 mM quercetin + 5 mM gallic acid + 5 mM cinnamic acid | 76.30 | 0.7630 | 0.8570 | −0.094 | AD |
| 5 mM quercetin + 5 mM gallic acid + 5 mM isorhamnetin | 75.06 | 0.7506 | 0.6764 | 0.074 | AD |
| 5 mM quercetin + 0.5 mM gallic acid + 5 mM isorhamnetin | 67.90 | 0.6790 | 0.7142 | −0.035 | AD |
| 5 mM quercetin + 5 mM gallic acid + 0.5 mM isorhamnetin | 82.45 | 0.8245 | 0.8262 | −0.002 | AD |
| 5 mM quercetin + 0.5 mM cinnamic acid + 0.5 mM isorhamnetin | 79.21 | 0.7921 | 0.8210 | −0.029 | AD |
| 5 mM quercetin + 5 mM cinnamic acid + 5 mM isorhamnetin | 67.90 | 0.6790 | 0.7301 | −0.051 | AD |
| 5 mM quercetin + 0.5 mM cinnamic acid + 5 mM isorhamnetin | 70.21 | 0.7021 | 0.6722 | 0.030 | AD |
| 5 mM quercetin + 5 mM ferulic acid + 5 mM isorhamnetin | 69.05 | 0.6905 | 0.7750 | −0.084 | AD |

Note:
SY is the synergistic effect; AD is the additive effect; and SU is the sub-additive effect.

TABLE 4

Effects of tyrosinase inhibitor consisting of four-component polyphenol on tyrosinase

| Tyrosinase inhibitor | Tyrosinase relative activity (%) | Vabcd | V*3 (Va × Vb × Vc × Vd) | Vabcd − V*3 | |
|---|---|---|---|---|---|
| 5 mM quercetin + 5 mM ferulic acid + 0.5 mM gallic acid + 0.5 mM cinnamic acid | 89.47 | 0.8947 | 0.9227 | −0.028 | AD |
| 5 mM quercetin + 5 mM ferulic acid + 5 mM gallic acid + 5 mM cinnamic acid | 98.89 | 0.9889 | 0.9492 | 0.040 | AD |
| 5 mM quercetin + 5 mM ferulic acid + 0.5 mM gallic acid + 5 mM cinnamic acid | 91.69 | 0.9169 | 1.0022 | −0.085 | AD |
| 5 mM quercetin + 5 mM ferulic acid + 5 mM gallic acid + 0.5 mM cinnamic acid | 99.17 | 0.9917 | 0.8738 | 0.118 | SU |
| 5 mM quercetin + 0.5 mM gallic acid + 0.5 mM cinnamic acid + 0.5 mM isorhamnetin | 87.26 | 0.8726 | 0.8380 | 0.035 | AD |
| 5 mM quercetin + 0.5 mM gallic acid + 0.5 mM cinnamic acid + 5 mM isorhamnetin | 81.72 | 0.8172 | 0.6861 | 0.131 | SU |
| 5 mM quercetin + 0.5 mM gallic acid + 5 mM cinnamic acid + 0.5 mM isorhamnetin | 86.70 | 0.8670 | 0.9103 | −0.043 | AD |
| 5 mM quercetin + 0.5 mM gallic acid + 5 mM cinnamic acid + 5 mM isorhamnetin | 81.16 | 0.8116 | 0.7452 | 0.066 | AD |
| 5 mM quercetin + 5 mM gallic acid + 0.5 mM cinnamic acid + 0.5 mM isorhamnetin | 91.41 | 0.9141 | 0.7937 | 0.120 | SU |
| 5 mM quercetin + 5 mM gallic acid + 0.5 mM cinnamic acid + 5 mM isorhamnetin | 84.21 | 0.8421 | 0.6498 | 0.192 | SU |
| 5 mM quercetin + 5 mM gallic acid + 5 mM cinnamic acid + 0.5 mM isorhamnetin | 92.80 | 0.9280 | 0.8621 | 0.066 | AD |
| 5 mM quercetin + 5 mM gallic acid + 5 mM cinnamic acid + 5 mM isorhamnetin | 83.93 | 0.8393 | 0.7058 | 0.134 | SU |

Note:
SY is the synergistic effect; AD is the additive effect; and SU is the sub-additive effect.

Comparative Example 2: Effect of Heating Treatment on Inhibition of Tyrosinase Activity by Tyrosinase Inhibitor 1. According to the method of Example 1, the difference is that the heating treatment is not performed, and other parameters are the same as those in Example 1, the determined tyrosinase relative activity is 78.82%, and the tyrosinase relative activity after the heating treatment is 33.62% (Example 1), which indicates that the heating treatment is beneficial to the inhibitory effect of the tyrosinase inhibitor on the tyrosinase.
2. According to the method of Example 1, the difference is that the heating temperature is set as 100° C., and other parameter conditions are the same as those in Example 1. The determined tyrosinase relative activity is 70.56%, while the tyrosinase relative activity after heating treatment at 150° C. is 33.62% (Example 1), which indicates that too low temperature will affect the effect of the tyrosinase inhibitor.
3. According to the method of Example 1, the difference is that the heating temperature is set as 200° C., and other parameters are the same as those in Example 1. The determined tyrosinase relative activity is 65.78%, and the tyrosinase relative activity after heating treatment at 150° C. is 33.62% (Example 1), which indicates that too high temperature will affect the effect of the tyrosinase inhibitor.

Although the disclosure has been provided as above in the preferred examples, it is not intended to limit the disclosure. Any person skilled in the art can make various changes and modifications without departing from the spirit and scope of the disclosure. Therefore, the protection scope of the disclosure should be defined by the claims.

What is claimed is:

1. A method for enhancing tyrosinase inhibitory activity, which comprises:
   heating a tyrosinase inhibitor,
   wherein the tyrosinase inhibitor consists of a phenolic acid and a saponin;
   wherein the phenolic acid consists of one of the following:
   (a) 5 mM quercetin, 5 mM cinnamic acid, and 5 mM ferulic acid;
   (b) 5 mM quercetin, 0.5 mM cinnamic acid, and 5 mM ferulic acid;
   (c) 5 mM quercetin, 0.5 mM gallic acid, and 5 mM ferulic acid;
   (d) 5 mM quercetin, 0.5 mM gallic acid, and 0.5 mM isorhamnetin;
   (e) 5 mM quercetin, 5 mM cinnamic acid, and 0.5 mM isorhamnetin; or
   (f) 5 mM quercetin, 5 mM ferulic acid, and 0.5 mM isorhamnetin;
   wherein the saponin is protodioscin or sarsasapogenin with a concentration of 0.5 mg/mL to 1.5 mg/ml; and
   wherein heating is performed at 130° C. to 170° C. for 30 minutes, and wherein the tyrosinase inhibitor synergistically increases tyrosinase inhibitory activity compared to a tyrosinase inhibitor when heated at a temperature outside of the 130° C. to 170° C. temperature range.

2. A tyrosinase inhibitor, wherein the tyrosinase inhibitor consists of a phenolic acid and a saponin;
   wherein the phenolic acid consists of one of the following:
   (a) 5 mM quercetin, 5 mM cinnamic acid, and 5 mM ferulic acid;
   (b) 5 mM quercetin, 0.5 mM cinnamic acid, and 5 mM ferulic acid;
   (c) 5 mM quercetin, 0.5 mM gallic acid, and 5 mM ferulic acid;
   (d) 5 mM quercetin, 0.5 mM gallic acid, and 0.5 mM isorhamnetin;
   (e) 5 mM quercetin, 5 mM cinnamic acid, and 0.5 mM isorhamnetin; or
   (f) 5 mM quercetin, 5 mM ferulic acid, and 0.5 mM isorhamnetin; and
   wherein the saponin is protodioscin or sarsasapogenin with a concentration of 0.5 mg/mL to 1.5 mg/mL.

3. The method according to claim 1, wherein the phenolic acid is selected from (a), (b), (d), (e), or (f), and wherein the saponin is protodioscin with a concentration of 0.5 mg/mL to 1.5 mg/mL.

4. The method according to claim 1, wherein the phenolic acid is (c) 5 mM quercetin, 0.5 mM gallic acid, and 5 mM ferulic acid, and wherein the saponin is sarsasapogenin with a concentration of 0.5 mg/mL to 1.5 mg/mL.

5. The method according to claim 1, wherein the phenolic acid is selected from (b), (d), (e), or (f), and wherein the saponin is protodioscin with a concentration of 0.5 mg/mL to 1.5 mg/mL.

6. The method according to claim 1, wherein the phenolic acid is (b) or (d), and wherein the saponin is protodioscin with a concentration of 0.5 mg/mL to 1.5 mg/mL.

7. The method according to claim 1, wherein the phenolic acid is selected from (a), (e), or (f), and wherein the saponin is protodioscin with a concentration of 0.5 mg/mL to 1.5 mg/mL.

8. The method according to claim 3, wherein the saponin is protodioscin with a concentration of 1.0 mg/mL.

9. The method according to claim 4, wherein the saponin is sarsasapogenin with a concentration of 1.5 mg/mL.

10. The method according to claim 5, wherein the saponin is protodioscin with a concentration of 1.0 mg/mL.

11. The method according to claim 6, wherein the saponin is protodioscin with a concentration of 1.0 mg/mL.

12. The method according to claim 7, wherein the saponin is protodioscin with a concentration of 1.0 mg/mL.

13. The tyrosinase inhibitor according to claim 2, wherein the phenolic acid is selected from (a), (b), (d), (e), or (f), and wherein the saponin is protodioscin with a concentration of 0.5 mg/mL to 1.5 mg/mL.

14. The tyrosinase inhibitor according to claim 2, wherein the phenolic acid is (c) 5 mM quercetin, 0.5 mM gallic acid, and 5 mM ferulic acid, and wherein the saponin is sarsasapogenin with a concentration of 0.5 mg/mL to 1.5 mg/mL.

15. The tyrosinase inhibitor according to claim 2, wherein the phenolic acid is selected from (b), (d), (e), or (f), and wherein the saponin is protodioscin with a concentration of 0.5 mg/mL to 1.5 mg/mL.

16. The tyrosinase inhibitor according to claim 2, wherein the phenolic acid is (b) or (d), and wherein the saponin is protodioscin with a concentration of 0.5 mg/mL to 1.5 mg/mL.

17. The tyrosinase inhibitor according to claim 2, wherein the phenolic acid is selected from (a), (e), or (f), and wherein the saponin is protodioscin with a concentration of 0.5 mg/mL to 1.5 mg/mL.

18. The tyrosinase inhibitor according to claim 13, wherein the saponin is protodioscin with a concentration of 1.0 mg/mL.

19. The tyrosinase inhibitor according to claim 14, wherein the saponin is sarsasapogenin with a concentration of 1.5 mg/mL.

20. The method according to claim 15, wherein the saponin is protodioscin with a concentration of 1.0 mg/mL.

* * * * *